(12) United States Patent
Takeshita et al.

(10) Patent No.: US 7,487,710 B2
(45) Date of Patent: Feb. 10, 2009

(54) HIGH-PRESSURE GENERATION APPARATUS

(75) Inventors: Nao Takeshita, Tsukuba (JP); Chieko Terakura, Tsukuba (JP); Hidenori Takagi, Tsukuba (JP); Yoshinori Tokura, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 363 days.

(21) Appl. No.: 11/212,567

(22) Filed: Aug. 29, 2005

(65) Prior Publication Data

US 2006/0045779 A1    Mar. 2, 2006

(30) Foreign Application Priority Data

Sep. 1, 2004    (JP)    ............................. 2004-254153

(51) Int. Cl.
*B01J 3/06* (2006.01)
*B30B 11/00* (2006.01)

(52) U.S. Cl. ....................................... 92/169.2; 425/77
(58) Field of Classification Search ................ 92/169.2; 425/77, 405.2
See application file for complete search history.

(56) References Cited

U.S. PATENT DOCUMENTS

| | | | | |
|---|---|---|---|---|
| 2,941,243 A | * | 6/1960 | Bundy | 425/77 |
| 2,941,244 A | * | 6/1960 | Wentorf, Jr. | 425/77 |
| 3,695,797 A | * | 10/1972 | Bakul et al. | 425/77 |
| 3,732,043 A | * | 5/1973 | Bakul et al. | 425/77 |
| 3,790,322 A | * | 2/1974 | Sirota et al. | 425/77 |
| 4,021,171 A | * | 5/1977 | Shulzhenko et al. | 425/77 |
| 4,196,181 A | * | 4/1980 | Vereschagin et al. | 425/77 |

(Continued)

FOREIGN PATENT DOCUMENTS

| JP | 62-277143 B2 | 12/1987 |
|---|---|---|
| JP | 10-101434 A | 4/1998 |

OTHER PUBLICATIONS

Nakanishi, T., Takeshita, N., and Mori, N. "A newly developed high-pressure cell by using modified Bridgman anvils for precise measurements in magnetic fields at low temperatures" Review of Scientific Instruments vol. 73, No. 4, Apr. 2002 pp. 1828-1831.*

*Primary Examiner*—Thomas E Lazo
(74) *Attorney, Agent, or Firm*—Sughrue Mion, PLLC

(57) ABSTRACT

Disclosed is a high-pressure generation apparatus, which comprises a pair of columnar-shaped anvils disposed in opposed relation to one another to define a pressure-generating space therebetween. The anvils are adapted to be applied with a load therebetween to generate a high pressure in the pressure-generating space. Each of the anvils has a top portion formed in an approximately circular truncated cone shape, and the top portion has a central region formed with a depression having a side surface which extends obliquely outward. The high-pressure generation apparatus also includes a cylindrical capsule disposed in a central area of the pressure-generating space, and a laminated member formed by alternately laminating a doughnut-shaped metallic thin plate and a doughnut-shaped insulating member along the outer periphery of the capsule. The improved shape of the depression makes it possible to significantly reduce damages of the components. In addition, the laminated member formed of the metallic thin plate and the insulating member originally used for sealing the pressure-generating space makes it possible to generate a higher pressure.

2 Claims, 4 Drawing Sheets

U.S. PATENT DOCUMENTS 4,220,677 A * 9/1980 Fedoseev et al. .............. 425/77
4,970,396 A * 11/1990 Wong ...................... 250/338.1
5,295,402 A * 3/1994 Bovenkerk ................... 425/77
6,543,295 B2 * 4/2003 Xu et al. ...................... 73/818

* cited by examiner

HIGH-PRESSURE GENERATION APPARATUS

TECHNICAL FIELD

The present invention relates to a high-pressure generation apparatus for generating a high pressure, and more particularly to a high-pressure generation apparatus designed to generate a high pressure in a pressure-generating space thereof and allowing an electrode or the like to be introduced inside the apparatus for a variety of purposes, such as measurement of various physical values and/or an internal temperature of a sample contained in the pressure-generating space, and heating of the sample.

BACKGROUND ART

FIG. 5 shows the structure of a piston-cylinder type high-pressure generation apparatus which is the most typical type as a conventional high-pressure generation apparatus, wherein FIG. 5(a) is a sectional front view thereof, and FIG. 5(b) is a sectional view taken along the line A-A in FIG. 5(a). This high-pressure generation apparatus is designed to insert a piston 102 into a cylindrical cylinder 101 and apply a load to the piston 102 from either side thereof so as to generate a high pressure in a high-pressure space 103. This high-pressure generation apparatus can be comprised of members made of a hard or stiff material to generate a pressure of up to about 30,000 atms. However, the high-pressure generation apparatus has difficulty in allowing a maximum possible pressure to be increased beyond a mechanical strength of the cylinder 101 and the piston 102, and consequently cannot generate a pressure out of the bounds of the mechanical strength. In order to break through this restriction, a high-pressure generation apparatus as disclosed in the following Non-Patent Publication 1 has been developed. This apparatus is an innovative technology capable of generating a high pressure of up to about 60,000 atms in spite of a compact structure.

[Non-Patent Publication 1] Nakanishi T, Takeshita N and Môri N, A newly developed high-pressure cell by using modified Bridgman anvils for precise measurements in magnetic fields at low temperature, Rev. Sci. Instrum., 73, 1828, (2002)

The high-pressure generation apparatus disclosed in the Non-Patent Publication 1 comprises a pair of approximately circular truncated cone-shaped components disposed in opposed relation to one another, and a pressure-generating component interposed between the opposed components. Differently from the aforementioned piston-cylinder type apparatus designed to use components in an elastic region thereof, the pressure-generating component is designed to be used in a plastic region thereof. Based on these components, this high-pressure generation apparatus has succeeded in drastically expanding an upper limit of possible pressure and enhancing the efficiency of pressure generation to a certain applied load while significantly downsizing the apparatus. Further, each of the opposed components has a top portion formed with a cylindrical-shaped depression having a side surface which extends uprightly or vertically. The formation of the depression makes it possible to drastically increase the volume of a pressure-generating space, and encapsulate a liquid inside the apparatus to allow a pressure to be isotropically generated.

However, a maximum possible pressure of this high-pressure generation apparatus is limited to about 60,000 atms, due to breakage of the components caused by stress concentration.

DISCLOSURE OF THE INVENTION

It is an object of the present invention to provide a high-pressure generation apparatus capable of significantly suppressing damages of components based on improvement in shape of the depression of the high-pressure generation apparatus disclosed in the Non-Patent Publication 1 while taking advantage of the basic structure thereof, and generating a higher pressure in a larger pressure-generating space defined by a cylindrical capsule and a laminated member used for sealing the space, wherein the cylindrical capsule is disposed in a central area of the space, and the laminated member is formed by alternately laminating a doughnut-shaped metallic thin plate and a doughnut-shaped insulating member along the outer periphery of the capsule.

The present invention employs the following solutions for solving the above problems.

In accordance with the first aspect of the present invention, a high-pressure generation apparatus which comprises a pair of columnar-shaped anvils disposed in opposed relation to one another to define a pressure-generating space therebetween, wherein the anvils are adapted to be applied with a load therebetween to generate a high pressure in the pressure-generating space. In this high-pressure generation apparatus, each of the anvils has a top portion formed in an approximately circular truncated cone shape, and the top portion has a central region formed with a depression having a side surface which extends obliquely outward.

In accordance with the second aspect of the present invention, the above high-pressure generation apparatus is provided with a cylindrical capsule disposed in a central area of the pressure-generating space, and a laminated member formed by alternately laminating a doughnut-shaped metallic thin plate and a doughnut-shaped insulating member along the outer periphery of the capsule.

According to the first aspect of the present invention, as to the shape of the depression formed in the central region of each top portion of the anvils, the conventional cylindrically-shaped depression having the vertically-extending side surface is changed to the depression having a side surface which extends obliquely outward. This improvement makes it possible to reduce a stress to be concentrated in the anvils during pressure generation and prevent the occurrence of damages in the anvils so as to allow a larger load to be applied between the anvils.

According to the second aspect of the present invention, the laminated member formed by alternately laminating a doughnut-shaped metallic thin plate and a doughnut-shaped insulating member along the outer periphery of the capsule in a multi-layered manner is employed as a sealing or gasket structure. The laminated member makes it possible to increase a vertically deformable amount of the pressure-generation space so as to allow the pressure-generation space to be compressed at a higher rate.

Other features and advantages of the present invention will be apparent from the accompanying drawings and from the detailed description.

BEST MODE FOR CARRYING OUT THE INVENTION

With reference to FIGS. 1 to 4, one embodiment of the present invention will be described.

Figure 1:
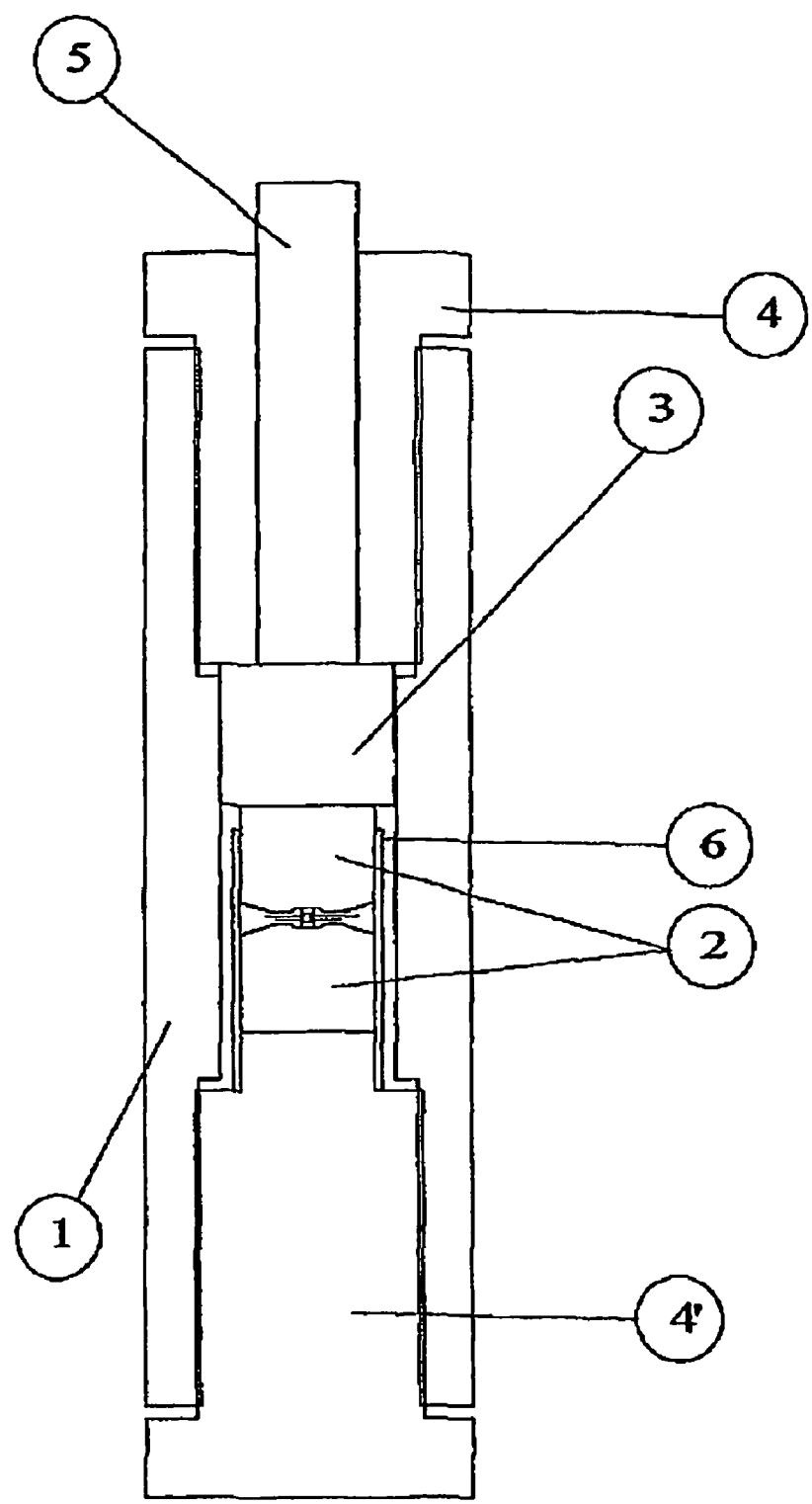
FIG. 1 is an overall view showing a high-pressure generation apparatus according to one embodiment of the present invention.
Figure 2:
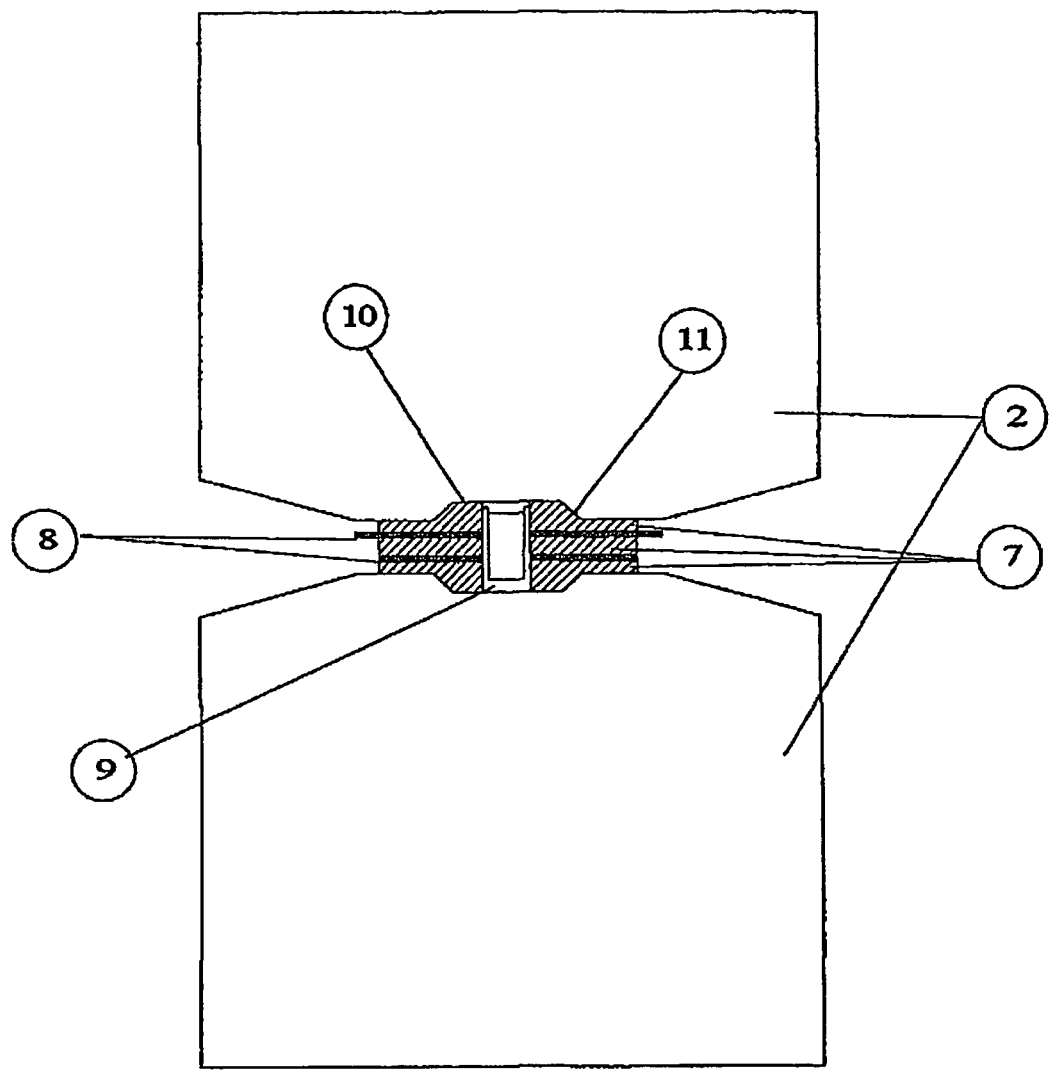
FIG. 2 is a fragmentary enlarged view showing a pressure-generating space defined between a pair of anvils 2 illustrated in FIG. 1.

FIG. 1 is an overall view showing a high-pressure generation apparatus according to the embodiment of the present invention. FIG. 2 is a fragmentary enlarged view showing a pressure-generating space defined between a pair of anvils 2 illustrated in FIG. 1, and FIG. 3 is a top plan view showing a metal gasket 8 illustrated in FIG. 2, viewing from a pressing direction.

In these figures, the reference numeral 1 indicates a cell body. The reference numeral 2 indicates a pair of columnar-shaped anvils disposed in opposed to one another. Each of the anvils 2 has a top portion formed in an approximately circular truncated cone shape. The reference numeral 3 indicates an anvil support. The reference numeral 4, 4' indicates a clamping nut. The reference numeral 5 indicates a pressing member, and the reference numeral 6 indicates a tubular member. The reference numeral 7 indicates a doughnut-shaped insulating gasket having a high hardness, and a reference numeral 8 indicates a doughnut-shaped metallic gasket having a high hardness. The reference numeral 9 indicates a capsule disposed in a pressure-generation space defined between the anvils 2, and adapted to allow a sample and a liquid pressure medium for transmitting a pressure to the sample and maintaining hydrostaticity or isotropy, to be encapsulated therein. The reference numeral 10 indicates a circular-shaped depression formed in the approximately circular truncated cone-shaped top portion of each of the anvils 2, and the reference numeral 11 indicates an annular-shaped side surface of the depression 10. The side surface 11 is formed to extend obliquely outward.

Figure 3A:
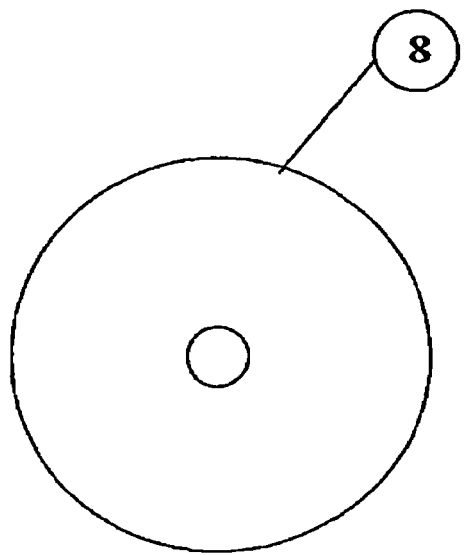
FIG. 3 is a top plan view showing a metal gasket 8 illustrated in FIG. 2, viewing from a pressing direction.
Figure 3B:
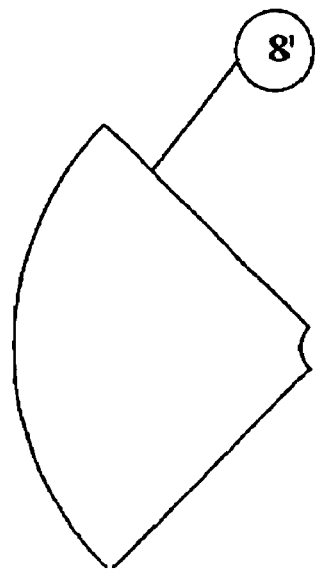

As shown in FIG. 2, a laminated member comprising the insulating gasket 7 and the metallic gasket 8 is disposed around the outer periphery of the capsule 9 to prevent pressure leakage. The insulating gasket 7 is a doughnut-shaped member having a central region formed with a through-hole for installing the capsule 9. The metallic gasket 8 may be a thin plate having a doughnut shape similar to that of the insulating gasket 7, as shown in FIG. 3(a), or may be a thin plate formed of a plurality of sector-shaped separate members, as shown in FIG. 3(b). As shown in FIG. 2, the insulating gasket 7 and the metallic gasket 8 are alternately laminated along the vertical direction in a multi-layered manner to form the laminated member having a central through-hole defined as a space for receiving the capsule 9 therein. In this embodiment, the laminated member is comprised of three tiers of the insulating gaskets 7 and two tiers of the metallic gaskets 8.

An operation of the high-pressure generation apparatus illustrated in FIG. 1 will be described below. Firstly, the pressure-generating portion as shown in FIG. 2 is assembled. Then, a lower portion of the apparatus is immovably fixed, and a certain load is applied vertically downward to an upper portion of the pressing member 5. In conjunction with the applied load, the upper anvil 2 is pressed vertically downward through the anvil support 3. The upper anvil 2 is guided by the tubular member 6 in such a manner as to be disposed in opposed relation to and in alignment with the lower anvil 2, and moved to gradually press the pressure-generating portion disposed in the central region of the apparatus. That is, by applying the load, the insulating gaskets 7 are deformed to allow a distance between the anvils 2 to be reduced. In this process, a frictional force acting between the metallic gasket 8 and the insulating gasket 7 prevents the pressure-generating space from being horizontally deformed. Thus, the pressure-generating space is compressed substantially only in the vertical direction to generate a large pressure in the inside of the capsule 9.

The metallic gasket 8 is also used for providing an electrical wiring in the inside of the capsule 9 to perform electrical measurement and/or heating of a sample contained in the capsule.

The load applied to the pressure-generating space is maintained by a screw engagement between the clamping nuts 4, 4' and corresponding opposite threaded ends of a cylindrical-shaped inner peripheral surface of the cell body 1. Specifically, after a pressure is generated by applying a certain load, the clamping nuts 4, 4' can be tightened to maintain the applied load so as to keep the generated pressure unchanged.

In this way, as to the shape of the depression 10 formed in the central region of each top portion of the anvils 2, the conventional cylindrically-shaped depression having the vertically-extending side surface is changed to the depression having the side surface 11 which extends obliquely outward. Thus, as compared to the conventional apparatus having a similar basic structure and generating an upper limit pressure of about 60,000 atms, as disclosed in the Non-Patent Publication 1, the high-pressure generation apparatus according to this embodiment can reduce a stress to be concentrated in the anvils 2 during pressure generation and prevent the occurrence of damages in the anvils 2 so as to allow a larger load to be applied between the anvils 2. In addition, the multi-layered gasket structure formed of the insulating gaskets 7 and the metallic gaskets 8 is employed. This makes it possible to increase a vertically deformable amount of the pressure-generation space so as to allow the pressure-generation space to be compressed at a higher rate.

Figure 4:
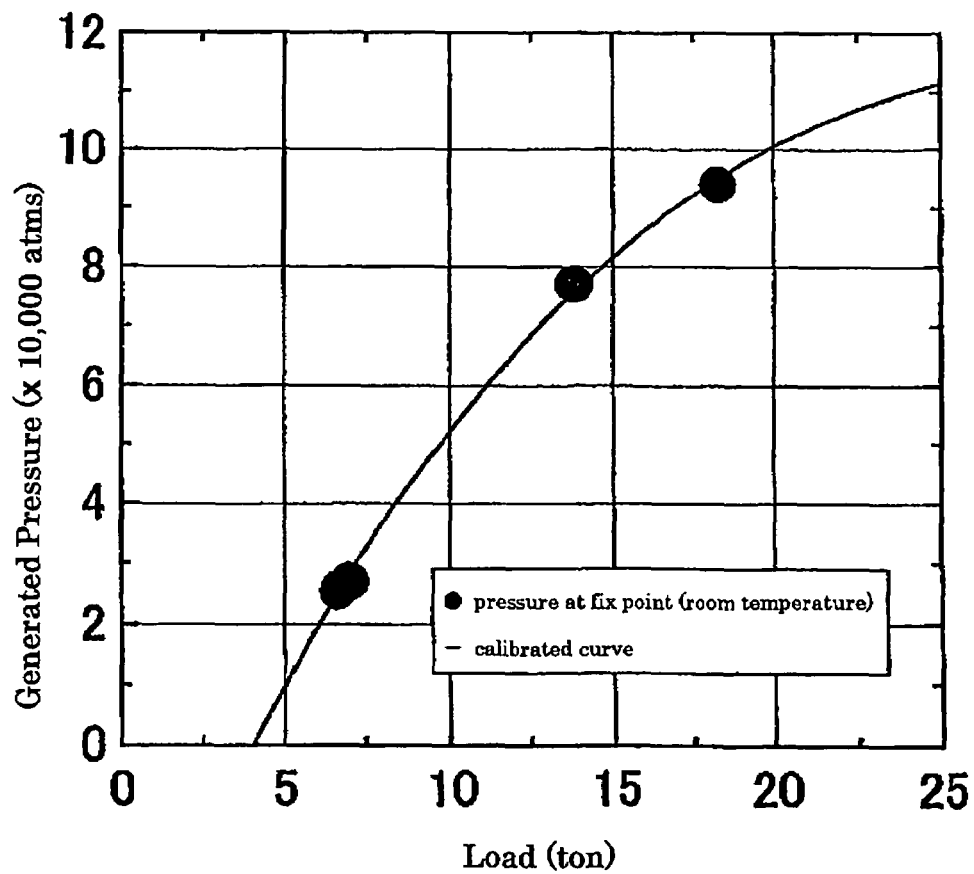
FIG. 4 is a graph showing an experimental result of the high-pressure generation apparatus according to the embodiment.
Figure 5:
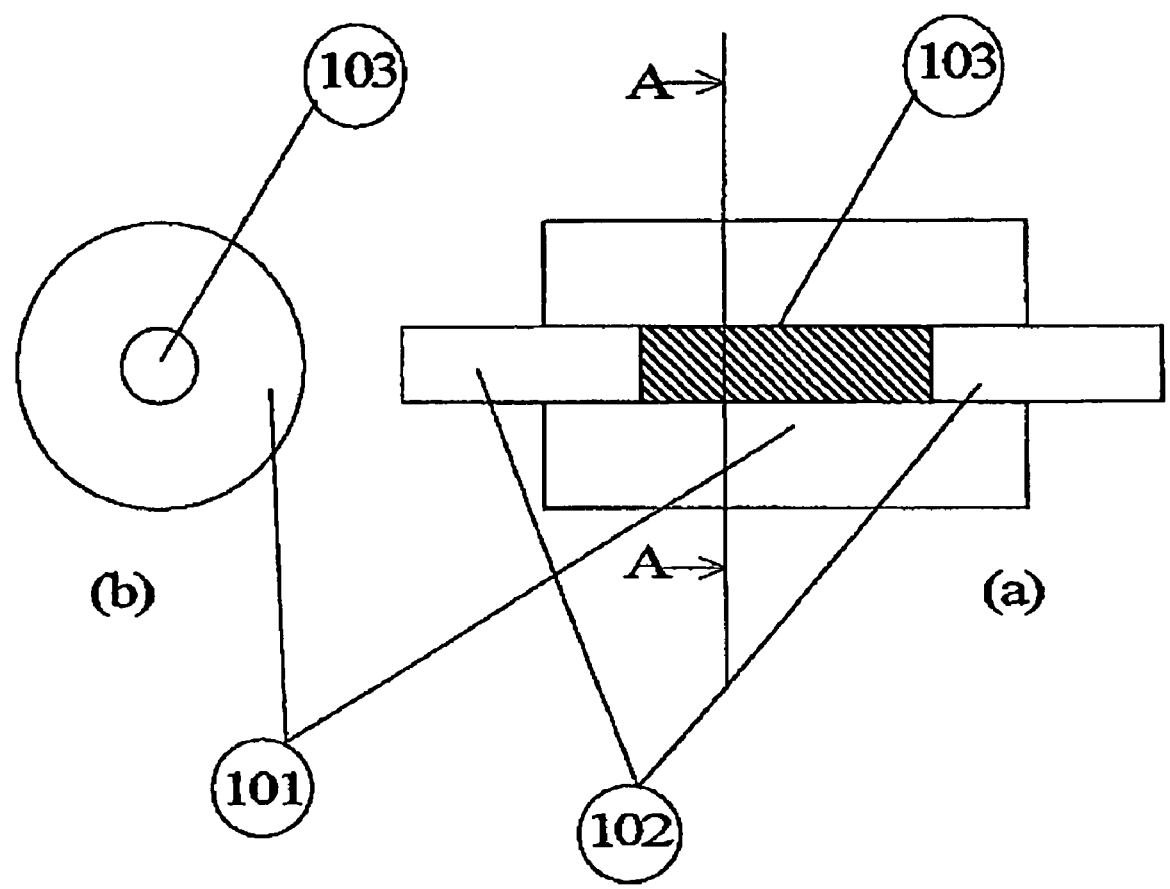
FIG. 5 is a schematic diagram showing a piston-cylinder type high-pressure generation apparatus which is the most typical type as a conventional high-pressure generation apparatus.

FIG. 4 is a graph showing an experimental result of the high-pressure generation apparatus according to this embodiment. In FIG. 4, the horizontal axis represents a load to be applied between the anvils 2 from the pressing member 5, and the vertical axis represents a pressure generated in the capsule 9.

As seen in FIG. 4, the high-pressure generation apparatus according to this embodiment can achieve a drastically enhanced performance as compared to the conventional apparatus as disclosed in the Non-Patent Publication 1, to provide a higher pressure, specifically a maximum possible pressure of 100,000 atms or more at room temperatures in rough figures.

An advantageous embodiment of the invention has been shown and described. It is obvious to those skilled in the art that various changes and modifications may be made therein without departing from the spirit and scope thereof as set forth in appended claims.

What is claimed is:

1. A high-pressure generation apparatus, comprising:
   a pair of columnar-shaped anvils disposed in opposed relation to one another;

a pressure-generating space defined between said anvils;

said anvils being adapted to be applied with a load therebetween to generate a high pressure in said pressure-generating space, wherein each of said anvils has a top portion formed in an approximately circular truncated cone shape, said top portion having a central region formed with a depression having a side surface which extends obliquely outward; and a laminated member surrounding the pressure-generating space and formed with a least two metallic thin plates and a plurality of insulating gaskets that are placed between the metallic thin plates and between the metallic thin plates and the anvils;

wherein the high-pressure generation apparatus produces a pressure in the pressure-generating space of approximately more than 60,000 atmospheres to approximately at least 100,000 atmospheres.

2. The high-pressure generation apparatus as defined in claim 1, which includes a cylindrical capsule disposed in a central area of said pressure-generating space, and a laminated member formed by alternately laminating a doughnut-shaped metallic thin plate and a doughnut-shaped insulating member along the outer periphery of said capsule.

* * * * *